United States Patent
Bebbington et al.

(10) Patent No.: US 8,168,183 B2
(45) Date of Patent: May 1, 2012

(54) ANTIBODIES TO GRANULOCYTE-MACROPHAGE COLONY-STIMULATING FACTOR

(75) Inventors: Christopher R. Bebbington, San Mateo, CA (US); Kenneth Luehrsen, Half Moon Bay, CA (US); Geoffrey T. Yarranton, Burlingame, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/431,661

(22) Filed: Apr. 28, 2009

(65) Prior Publication Data

US 2009/0274706 A1 Nov. 5, 2009

Related U.S. Application Data

(60) Provisional application No. 61/048,522, filed on Apr. 28, 2008.

(51) Int. Cl.
*A61K 39/395* (2006.01)
*C07K 16/00* (2006.01)
(52) U.S. Cl. ............... 424/133.1; 424/158.1; 530/389.2
(58) Field of Classification Search ............... 424/133.1, 424/158.1; 530/389.2
See application file for complete search history.

(56) References Cited

U.S. PATENT DOCUMENTS

| | | | |
|---|---|---|---|
| 7,381,801 | B2 | 6/2008 | Renner et al. |
| 2004/0053365 | A1 | 3/2004 | Renner et al. |
| 2005/0255552 | A1 | 11/2005 | Flynn et al. |
| 2006/0134098 | A1 | 6/2006 | Bebbington et al. |
| 2006/0228358 | A1 | 10/2006 | Lawson et al. |
| 2008/0095767 | A1 | 4/2008 | Jennings et al. |
| 2008/0187966 | A1 | 8/2008 | Simmons |
| 2008/0206241 | A1 | 8/2008 | Bebbington et al. |
| 2009/0263387 | A1* | 10/2009 | Bebbington et al. ........ 424/133.1 |
| 2010/0215650 | A1* | 8/2010 | Bebbington et al. ........ 424/133.1 |

FOREIGN PATENT DOCUMENTS

| | | | |
|---|---|---|---|
| EP | 1530580 A2 | | 5/2005 |
| WO | WO 03/068920 A2 | | 8/2003 |
| WO | WO 2004/003019 | * | 6/2004 |
| WO | WO 2006/111353 A2 | | 10/2006 |
| WO | WO 2006/122797 A2 | | 11/2006 |
| WO | WO 2009/038760 A2 | | 3/2009 |

OTHER PUBLICATIONS

MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Dufner (Trends Biotechnol. 24(11):523-29 (2006)).*
Schoonbroodt, S., et al., "Oligonucleotide-assisted cleavage and ligation: a novel directional DNA cloning technology to capture cDNAs. Application in the construction of a human immune antibody phage-display library," *Nucleic Acids Research*, vol. 33, No. 9, e81, 14 pgs (2005).

* cited by examiner

*Primary Examiner* — Lynn Bristol
(74) *Attorney, Agent, or Firm* — Kilpatrick Townsend & Stockton LLP

(57) ABSTRACT

The current invention relates to high-affinity antibodies to Granulocyte-Macrophage Colony-Stimulating Factor that have reduced immunogenicity when administered to a human to treat diseases and method of using such antibodies.

36 Claims, 5 Drawing Sheets

FIGURE 1

```
VH1 1-02  QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR-----------------
VH#1      QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCVRRDRFPYYFDYWGQGTLVTVSS

VH1 1-03  QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAR-----------------
VH#2      QVQLVQSGAEVKKPGASVKVSCKASGYSFTNYYIEHWVRQAPGQRLEWMGWINAGNGNTKYSQKFQGRVAITRDTSASTAYMELSSLRSEDTAVYYCARRDRFPYYFDYWGQGTLVTVSS
VH#3      QVQLVQSGAEVKKPGASVKVSCKASGYSFTNYYIHHWVRQAPGQRLEWMGWINAGNGNTKYSQKFQGRVAITRDTSASTAYMELSSLRSEDTAVYYCARRQRFPYYFDYWGQGTLVTVSS
VH#4      QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCVRRQRFPYYFDYWGQGTLVTVSS
VH#5      QVQLVQSGAEVKKPGASVKVSCKASGYSFTNYYIHWVRQAPGQRLEWMGWINAGNGNTKYSQKFQGRVTITRDTSASTAYMELSSLRSEDTAVYYCVRRQRFPYYFDYWGQGTLVTVSS

VKIII A27 EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP----------
VK#1      EIVLTQSPATLSVSPGERATLSCRASQSVGTN-VAWYQQKPGQAPRVLIYSTSSRATGITDRFSGSGSGTDFTLTISRLEPEDFAVYYCQQFNRSPLTFGGGTKVEIK
VK#2      EIVLTQSPATLSVSPGERATLSCRASQSVGTN-VAWYQQKPGQAPRVLIYSTSSRATGITDRFSGSGSGTDFTLTISRLEPEDFAVYYCQQFNRSPLTFGGGTKVEIK
VK#3      EIVLTQSPATLSVSPGERATLSCRASQSIGSN-LAWYQQKPGQAPRVLIYSTSSRATGITDRFSGSGSGTDFTLTISRLEPEDFAVYYCQQFNRSPLTFGGGTKVEIK
VK#4      EIVLTQSPATLSVSPGERATLSCRASQSIGSN-LAWYQQKPGQAPRVLIYSTSSRATGITDRFSGSGSGTDFTLTISRLEPEDFAVYYCQQFNKSPLTFGGGTKVEIK
```

| Fab | Vh | Vk | Dissociation rate for binding to GM-CSF determined by surface plasmon resonance analysis (s$^{-1}$) |
|---|---|---|---|
| FB42-8  | #2 | #3 | $1.36 \times 10^{-4}$ |
| FB44-5  | #1 | #3 | $8.0 \times 10^{-5}$ |
| FB77-2  | #3 | #1 | $5.57 \times 10^{-5}$ |
| FB92-1  | #4 | #4 | $3.84 \times 10^{-5}$ |
| FB94-1  | #4 | #2 | $3.12 \times 10^{-5}$ |
| FB104-1 | #5 | #1 | $3.57 \times 10^{-5}$ |
| FB106-1 | #5 | #2 | $5.4 \times 10^{-5}$ |

ANTIBODIES TO GRANULOCYTE-MACROPHAGE COLONY-STIMULATING FACTOR

CROSS-REFERENCE TO RELATED APPLICATIONS

This application claims benefit of U.S. provisional application No. 61/048,522, filed Apr. 28, 2008, which application is herein incorporated by reference.

BACKGROUND OF THE INVENTION

"Granulocyte Macrophage-Colony Stimulating Factor" (GM-CSF) is a small glycoprotein that is produced in response to a number of inflammatory mediators by cells present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages and inhibits apoptosis of granulocytes and macrophages.

GM-CSF has been proposed to play a role in the pathogenesis of a number of diseases. There is therefore a need for additional therapies that target GM-CSF. The current invention provides improved anti-GM-CSF antibodies, e.g., for the treatment of diseases in which GM-CSF is part of the pathogenic mechanism.

BRIEF SUMMARY OF THE INVENTION

In one aspect, the invention provides anti-GM-CSF antibodies, e.g., humaneered antibodies, and methods of using such antibodies for the treatment of diseases for which it is desirable to inhibit GM-CSF receptor signaling. Thus, in some embodiments, the invention provides an anti-GM-CSF antibody, comprising a heavy chain variable region that comprises a CDR3 binding specificity determinant RQRFPY (SEQ ID NO:12) or RDRFPY (SEQ ID NO:13), a J segment, and a V-segment, wherein the J-segment comprises at least 95% identity to human JH4 (YFDYWGQGTLVTVSS; SEQ ID NO:14) and the V-segment comprises at least 90% identity to a human germ line VH1 1-02 or VH1 1-03 sequence; or a heavy chain variable region that comprises a CDR3 binding specificity determinant comprising RQRFPY (SEQ ID NO:12). In some embodiments, the J segment comprises YFDYWGQGTLVTVSS (SEQ ID NO:14). In some embodiments, the CDR3 comprises RQRFPYYFDY (SEQ ID NO:15) or RDRFPYYFDY (SEQ ID NO:16). In some embodiments, the heavy chain variable region CDR1 or CDR2 can be a human germline VH1 sequence; or both the CDR1 and CDR2 can be human germline VH1. In some embodiments, the antibody comprises a heavy chain variable region CDR1 or CDR2, or both CDR1 and CDR2, as shown in a $V_H$ region set forth in FIG. 1. In some embodiments, an antibody of the invention as a V-segment that has a $V_H$ V-segment sequence shown in FIG. 1. In some embodiments, an antibody of the invention comprises a $V_H$ that has the sequence of VH#1, VH#2, VH#3, VH#4, or VH#5 set forth in FIG. 1.

The invention also provides an anti-GM-CSF antibody, e.g., that has a heavy chain variable region as described in the paragraph above, where the antibody comprises a light chain variable region that comprises a CDR3 binding specificity determinant FNK or FNR. In some embodiments, such an antibody comprises a human germline JK4 region. In some embodiments, the antibody $V_L$ region CDR3 comprises QQFN(K/R)SPLT (SEQ ID NO:17), e.g., QQFNKSPLT (SEQ ID NO:18). In some embodiments, the light chain variable region comprises a CDR1, or a CDR2, or both a CDR1 and CDR2, of a $V_L$ region shown in FIG. 1. In some embodiments, the $V_L$ region comprises a V segment that has at least 95% identity to the VKIIIA27 V-segment sequence as shown in FIG. 1. In some embodiments, the $V_L$ region has the sequence of VK#1, VK#2, VK#3, or VK#4 set forth in FIG. 1.

In some embodiments, an antibody of the invention, e.g., that has a $V_H$ region sequence selected from the $V_H$ region sequences in FIG. 1 and a $V_L$ region selected from the $V_L$ region sequences in FIG. 1, have a monovalent affinity better than about 10 nM, and often better (less) than about 500 pM or better than about 50 pM as determined by surface plasmon resonance analysis performed at 37° C. Thus, in some embodiments, the antibodies of the invention have an affinity (as measured using surface plasmon resonance), of less than 50 pM, typically less than about 25 pM, or even less than 10 pM. In some embodiments, an anti-GM-CSF of the invention has a slow dissociation rate with a dissociation rate constant (kd) determined by surface plasmon resonance analysis at 37° C. for the monovalent interaction with GM-CSF less than approximately $10^{-4}$ s$^{-1}$, preferably less than $5\times10^{-5}$ s$^{-1}$ and most preferably less than $10^{-5}$ s$^{-1}$. In some embodiments, an antibody of the invention has a dissociation rate that is at least 2 to 3-fold slower than a reference chimeric c19/2 monoclonal antibody assayed under the same conditions, but has a potency that is at least 6-10 times greater than that of the reference antibody in neutralizing GM-CSF activity in a cell-based assay that measures GM-CSF activity.

In some embodiments, an antibody of the invention having a heavy chain variable region and/or a light chain variable region as described herein is an IgG. In some embodiments, the heavy chain has a constant region that has the amino acid sequence of SEQ ID NO:11. In some embodiments, the light chain constant region is a kappa light chain having a sequence set forth in SEQ ID NO:10. In some embodiments, an antibody of the invention has a heavy chain constant region as set forth in SEQ ID NO:11, a light chain kappa constant region having a sequence as set forth in SEQ ID NO:10 and a heavy chain and light chain variable region selected from the heavy and light chain variable regions shown in FIG. 1, e.g., the antibody heavy and light chain variable regions comprise one of the following combinations from the sequences set forth in FIG. 1: a) VH#2, VK#3; b) VH#1, VK#3; c) VH#3, VK#1; d) VH#4, VK#3; e) VH#4, VK#4; f) VH#4, VK#2; g) VH#5, VK#1; h) VH#5, VK#2; i) VH#3, VK#4; or j) VH#3, VL#3). One of skill will recognize that antibodies of the invention can be selected from any of the combinations of $V_H$ and $V_L$ regions set forth in FIG. 1 in conjunction with the teachings herein.

In some embodiments, the $V_H$ region sequence or $V_L$ region sequence, or both the $V_H$ and $V_L$ region amino acid sequences, comprise a methionine at the N-terminus.

In additional aspects, the invention provides a method of treating a patient that has a disease in which it is desirable to inhibit GM-CSF, the method comprising administering an antibody of any one of the preceding claims to the patient in a therapeutically effective amount. In some embodiments, the patient has osteopenia, rheumatoid arthritis, asthma, multiple sclerosis, psoriasis, chronic obstructive pulmonary disease, idiopathic thrombocytopenia purpura, Alzheimer's disease, heart failure, cardiac damage due to an ischemic event, or diabetes.

BRIEF DESCRIPTION OF THE DRAWINGS

FIG. 1 provides exemplary $V_H$ (SEQ ID NOS:1-5) and $V_L$ (SEQ ID NOS:6-9) sequences of anti-GM-CSF antibodies. VH1 1-02=SEQ ID NO:19; VH1 1-03=SEQ ID NO:20; VKIII A27=SEQ ID NO:21.

DETAILED DESCRIPTION OF THE INVENTION

Figure 2:
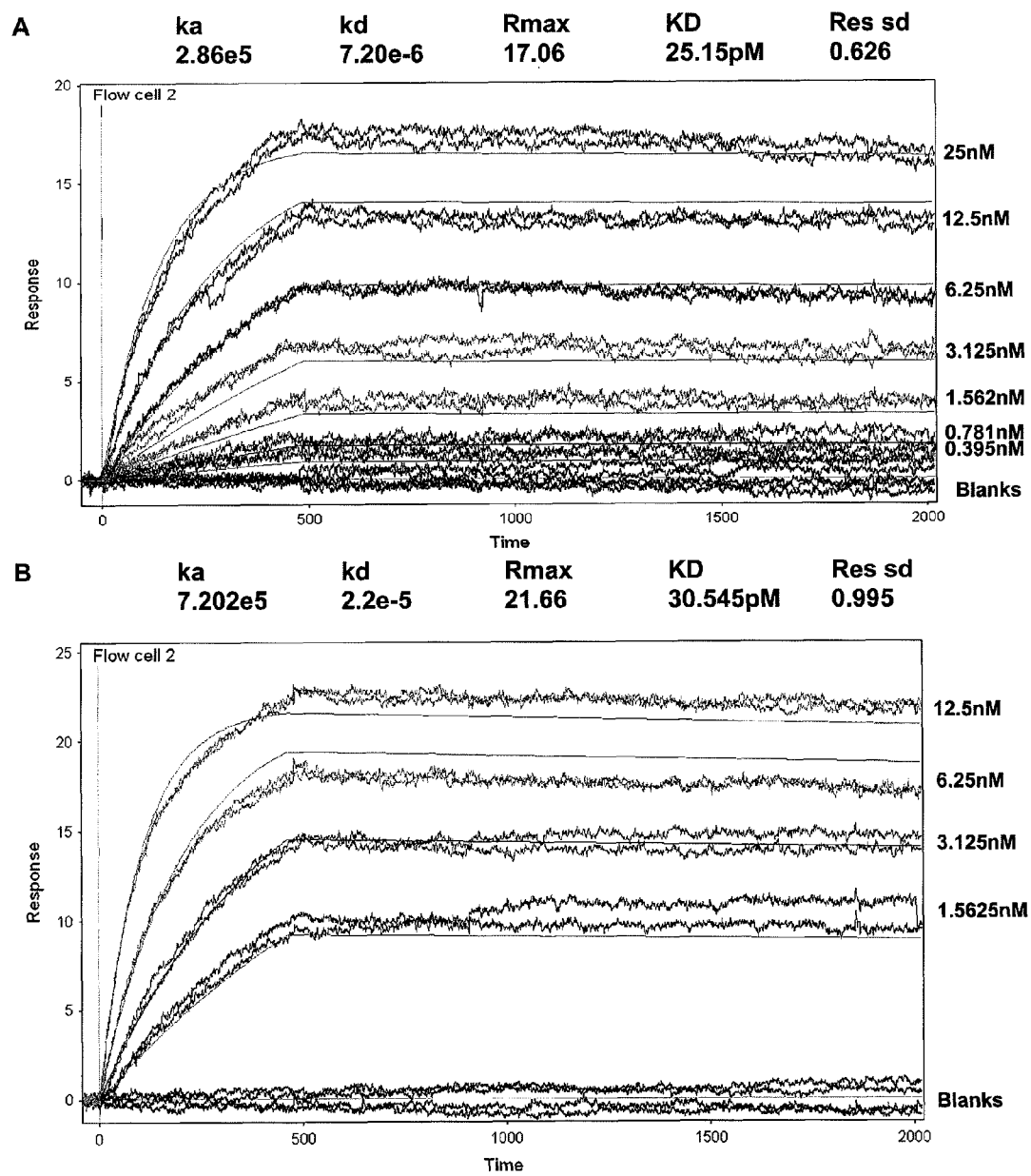
FIG. 2. Binding of GM-CSF to Ab1 (A) or Ab2 (B) determined by surface plasmon resonance analysis at 37° C. (Biacore 3000). Ab1 and Ab2 were captured on anti Fab polyclonal antibodies immobilized on the Biacore chip. Different concentrations of GM-CSF were injected over the surface as indicated. Global fit analysis was carried out assuming a 1:1 interaction using Scrubber2 software.

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term "antibody" as used herein also includes antibody fragments that retain binding specificity. For example, there are a number of well characterized antibody fragments. Thus, for example, pepsin digests an antibody C-terminal to the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo by utilizing recombinant DNA methodology or chemically. Thus, the term "antibody", as used here includes antibody fragments either produced by the modification of whole antibodies or synthesized using recombinant DNA methodologies.

Antibodies as used here also include various $V_H$-$V_L$ pair formats, including single chain antibodies (antibodies that exist as a single polypeptide chain), e.g., single chain Fv antibodies (sFv or scFv), in which a variable heavy and a variable light region are joined together (directly or through a peptide linker) to form a continuous polypeptide. The single chain Fv antibody is a covalently linked $V_H$-$V_L$ that may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. An antibody can also be in another fragment form, such as a disulfide-stabilized Fv (dsFv). Other fragments can also be generated, e.g., using recombinant techniques, as soluble proteins or as fragments obtained from display methods. Antibodies can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies for use in the current invention additionally include single domain antibodies (dAbs) and nanobodies (see, e.g., Cortez-Retamozo, et al., *Cancer Res.* 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. An endogenous J-segment is encoded by an immunoglobulin J-gene.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res*. January 1; 29(1): 207-9 (2001); MacCallum et al, Antibody-antigen interactions: Contact analysis and binding site topography, *J. Mol. Biol.*, 262 (5), 732-745 (1996); and Martin et al, *Proc. Natl. Acad. Sci.* USA, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "binding specificity determinant" or "BSD" as used in the context of the current invention refers to the minimum contiguous or non-contiguous amino acid sequence within a CDR region necessary for determining the binding specificity of an antibody. In the current invention, the minimum binding specificity determinants reside within a portion or the full-length of the CDR3 sequences of the heavy and light chains of the antibody.

As used herein, "anti-GM-CSF antibody" or "GM-CSF antibody" are used interchangeably to refer to an antibody that binds to GM-CSF and inhibits GM-CSF receptor activity. Such antibodies may be identified using any number of art-recognized assays that assess GM-CSF binding and/or function. For example, binding assays such as ELISA assays that measure the inhibition of GM-CSF binding to the alpha receptor subunit may be used. Cell-based assays for GM-CSF receptor signaling, such as assays which determine the rate of proliferation of a GM-CSF-dependent cell line in response to a limiting amount of GM-CSF, are also conveniently employed, as are assays that measure amounts of cytokine production, e.g., IL-8 production, in response to GM-CSF exposure.

As used herein, "neutralizing antibody" refers to an antibody that binds to GM-CSF and inhibits signaling by the GM-CSF receptor, or inhibits binding of GM-CSF to its receptor.

As used herein, "Granulocyte Macrophage-Colony Stimulating Factor" (GM-CSF) refers to a small naturally occurring glycoprotein with internal disulfide bonds having a molecular weight of approximately 23 kDa. In humans, it is encoded by a gene located within the cytokine cluster on human chromosome 5. The sequence of the human gene and protein are known. The protein has an N-terminal signal sequence, and a C-terminal receptor binding domain (Rasko and Gough In: The Cytokine Handbook, A. Thomson, et al, Academic Press, New York (1994) pages 349-369). Its three-dimensional structure is similar to that of the interleukins, although the amino acid sequences are not similar. GM-CSF is produced in response to a number of inflammatory mediators present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages and inhibits apoptosis of granulocytes and macrophages.

The term "equilibrium dissociation constant" or "affinity" abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any known method in the art. The antibodies of the present invention are high affinity antibodies. Such antibodies have a monovalent affinity better (less) than about 10 nM, and often better than about 500 pM or better than about 50 pM as determined by surface plasmon resonance analysis performed at 37° C. Thus, in some embodiments, the antibodies of the invention have an affinity (as measured using surface plasmon resonance), of less than 50 pM, typically less than about 25 pM, or even less than 10 pM.

In some embodiments, an anti-GM-CSF of the invention has a slow dissociation rate with a dissociation rate constant (kd) determined by surface plasmon resonance analysis at 37° C. for the monovalent interaction with GM-CSF less than approximately 10$^{-4}$ s$^{-1}$, preferably less than 5×10$^{-5}$ s$^{-1}$ and most preferably less than 10$^{-5}$ S$^{-1}$.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., Nature 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol.*

*Immunol.* 43: 1243, 2006; and Roguska et al., *Proc. Natl. Acad. Sci. USA* 91: 969, 1994).

A "humaneered" antibody in the context of this invention refers to an engineered human antibody having a binding specificity of a reference antibody. A "humaneered" antibody for use in this invention has an immunoglobulin molecule that contains minimal sequence derived from a donor immunoglobulin. Typically, an antibody is "humaneered" by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for humaneering are provided in US patent application publication no. 20050255552 and US patent application publication no. 20060134098.

A "human" antibody as used herein encompasses humanized and humaneered antibodies, as well as human monoclonal antibodies that are obtained using known techniques.

The term "hybrid" when used with reference to portions of a nucleic acid or protein, indicates that the nucleic acid or protein comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a hybrid protein refers to two or more subsequences that are not normally found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody binds to the antigen of interest, e.g., GM-CSF, with an affinity that is at least 100-fold better than its affinity for other antigens.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables and substitution matrices such as BLOSUM providing functionally similar amino acids are well known in the art. Such conservatively modified variants are in addition to and do not exclude polymorphic variants, interspecies homologs, and alleles of the invention. Typical conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

I. Introduction

The invention relates to antibodies that bind with high affinity to GM-CSF and are antagonists of GM-CSF. The antibodies comprise variable regions with a high degree of identity to human germ-line $V_H$ and $V_L$ sequences. In preferred embodiments, the BSD sequence in CDRH3 of an antibody of the invention comprises the amino acid sequence RQRFPY (SEQ ID NO:12) or RDRFPY (SEQ ID NO:13). The BSD in CDRL3 comprises FNK or FNR.

Complete V-regions are generated in which the BSD forms part of the CDR3 and additional sequences are used to complete the CDR3 and add a FR4 sequence. Typically, the portion of the CDR3 excluding the BSD and the complete FR4 are comprised of human germ-line sequences. In some embodiments, the CDR3-FR4 sequence excluding the BSD differs from human germ-line sequences by not more than 2 amino acids on each chain. In some embodiments, the J-segment comprises a human germline J-segment. Human germline sequences can be determined, for example, through the publicly available international ImMunoGeneTics database (IMGT) and V-base (on the worldwide web at vbase.mrc-cpe.cam.ac.uk).

The human germline V-segment repertoire consists of 51 heavy chain V-regions, 40κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, also Chothia et al., 1992, J Mol Biol 227:776-798; Tomlinson et al., 1995, EMBO J 14:4628-4638; and Williams et al., 1996, J Mol Biol 264:220-232).

Antibodies or antibodies fragments as described herein can be expressed in prokaryotic or eukaryotic microbial systems or in the cells of higher eukaryotes such as mammalian cells.

An antibody that is employed in the invention can be in any format. For example, in some embodiments, the antibody can be a complete antibody including a constant region, e.g., a human constant region, or can be a fragment or derivative of a complete antibody, e.g., a Fab, Fab', F(ab')$_2$, scFv, Fv, or a single domain antibody, such as a nanobody or a camelid antibody.

II. Heavy Chains

A heavy chain of an anti-GM-CSF antibody of the invention comprises a heavy-chain V-region that comprises the following elements:

1) human heavy-chain V-segment sequences comprising FR1-CDR1-FR2-CDR2-FR3

2) a CDRH3 region comprising the amino acid sequence R(Q/D)RFPY (SEQ ID NO:22)

3) a FR4 contributed by a human germ-line J-gene segment.

Examples of V-segment sequences that support binding to GM-CSF in combination with a CDR3-FR4 segment described above together with a complementary $V_L$ region are shown in FIG. 1. The V-segments can be, e.g., from the human VH1 subclass. In some embodiments, the V-segment is a human $V_H1$ sub-class segment that has a high degree of amino-acid sequence identity, e.g., at least 80%, 85%, or 90% or greater identity, to the germ-line segment VH1 1-02 or VH1 1-03. In some embodiments, the V-segment differs by not more than 15 residues from VH1 1-02 or VH1 1-03 and preferably not more than 7 residues.

The FR4 sequence of the antibodies of the invention is provided by a human JH1, JH3, JH4, JH5 or JH6 gene germ-line segment, or a sequence that has a high degree of amino-acid sequence identity to a human germline JH segment. In some embodiments, the J segment is a human germline JH4 sequence.

The CDRH3 also comprises sequences that are derived from a human J-segment. Typically, the CDRH3-FR4 sequence excluding the BSD differs by not more than 2 amino acids from a human germ-line J-segment. In typical embodiments, the J-segment sequences in CDRH3 are from the same J-segment used for the FR4 sequences. Thus, in some embodiments, the CDRH3-FR4 region comprises the BSD and a complete human JH4 germ-line gene segment. An exemplary combination of CDRH3 and FR4 sequences is shown below (SEQ ID NO:23), in which the BSD is in bold and human germ-line J-segment JH4 residues are underlined:

<u>CDR3</u>
R (Q/D) RFPY<u>YFDYWGQGTLVTVSS</u>

In some embodiments, an antibody of the invention comprises a V-segment that has at least 90% identity, or at least 91%, 92% 93%, 94%, 95%, 96%, 97%, 98%, 99%, or 100% identity to the germ-line segment VH 1-02 or VH1-03; or to one of the V-segments of the $V_H$ regions shown in FIG. 1, such as a V-segment portion of VH#1, VH#2, VH#3, VH#4, or VH#5.

In some embodiments, the V-segment of the $V_H$ region has a CDR1 and/or CDR2 as shown in FIG. 1. For example, an antibody of the invention may have a CDR1 that has the sequence GYYMH (SEQ ID NO:24) or NYYIH (SEQ ID NO:25); or a CDR2 that has the sequence WINPNSGGT-NYAQKFQG (SEQ ID NO:26) or WINAGNGNTKYSQK-FQG (SEQ ID NO:27).

In particular embodiments, an antibody has both a CDR1 and a CDR2 from one of the $V_H$ region V-segments shown in FIG. 1 and a CDR3 that comprises R(Q/D)RFPY (SEO ID NO:22), e.g., RDRFPYYFDY (SEQ ID NO:16) or RQRF-PYYFDY (SEQ ID NO:15). Thus, in some embodiments, an anti-GM-CSF antibody of the invention, may for example, have a CDR3-FR4 that has the sequence R(Q/D)RFPYY-FDYWGQGTLVTVSS (SEQ ID NO:23) and a CDR1 and/or CDR2 as shown in FIG. 1.

In some embodiments, a $V_H$ region of an antibody of the invention has a CDR3 that has a binding specificity determinant R(Q/D)RFPY (SEQ ID NO:22), a CDR2 from a human germline VH1 segment or a CDR1 from a human germline VH1. In some embodiments, both the CDR1 and CDR2 are from human germline VH1 segments.

III. Light Chains

A light chain of an anti-GM-CSF antibody of the invention comprises at light-chain V-region that comprises the following elements:

1) human light-chain V-segment sequences comprising FR1-CDR1-FR2-CDR2-FR3

2) a CDRL3 region comprising the sequence FNK or FNR, e.g., QQFNRSPLT (SEQ ID NO:28) or QQFNKSPLT (SEQ ID NO:18).

3) a FR4 contributed by a human germ-line J-gene segment. The $V_L$ region comprises either a Vlambda or a Vkappa V-segment. An example of a Vkappa sequence that supports binding in combination with a complementary $V_H$-region is provided in FIG. 1.

The $V_L$ region CDR3 sequence comprises a J-segment derived sequence. In typical embodiments, the J-segment sequences in CDRL3 are from the same J-segment used for FR4. Thus, the sequence in some embodiments may differ by not more than 2 amino acids from human kappa germ-line V-segment and J-segment sequences. In some embodiments, the CDRL3-FR4 region comprises the BSD and the complete human JK4 germline gene segment. Exemplary CDRL3-FR4 combinations for kappa chains are shown below in which the minimal essential binding specificity determinant is shown in bold and JK4 sequences are underlined:

<u>CDR3</u>
QQFNRS<u>PLTFGGGTKVEIK</u>

QQFNKS<u>PLTFGGGTKVEIK</u>

The Vkappa segments are typically of the VKIII sub-class. In some embodiments, the segments have at least 80% sequence identity to a human germline VKIII subclass, e.g., at least 80% identity to the human germ-line VKIIIA27 sequence. In some embodiments, the Vkappa segment may differ by not more than 18 residues from VKIIIA27. In other embodiments, the $V_L$ region V-segment of an antibody of the invention has at least 85% identity, or at least 90%, 91%, 92%, 93%, 94%, 95%, 96%, 97%, 98%, 99%, or 100% identity to the human kappa V-segment sequence of a $V_L$ region shown in FIG. 1, for example, the V-segment sequence of VK#1, VK#2, VK#3, or VK#4.

In some embodiments, the V-segment of the $V_L$ region has a CDR1 and/or CDR2 as shown in FIG. 1. For example, an antibody of the invention may have a CDR1 sequence of RASQSVGTNVA (SEQ ID NO:31) or RASQSIGSNLA (SEQ ID NO:32); or a CDR2 sequence STSSRAT (SEQ ID NO:33).

In particular embodiments, an anti-GM-CSF antibody of the invention may have a CDR1 and a CDR2 in a combination as shown in one of the V-segments of the $V_L$ regions set forth in FIG. 1 and a CDR3 sequence that comprises FNK or FNR, e.g., the CDR3 may be QQFNKSPLT (SEQ ID NO:18) or QQFNRSPLT (SEQ ID NO:28). In some embodiments, such a GM-CSF antibody may comprise an FR4 region that is FGGGTKVEIK (SEQ ID NO:34). Thus, an anti-GM-CSF antibody of the invention, can comprise, e.g., both the CDR1 and CDR2 from one of the $V_L$ regions shown in FIG. 1 and a CDR3-FR4 region that is FGGGTKVEIK (SEQ ID NO:34).

IV. Preparation of GM-CSF Antibodies

An antibody of the invention may comprise any of the $V_H$ regions VH#1, VH#2, VH#3, VH#4, or VH#5 as shown in FIG. 1. In some embodiment, an antibody of the invention may comprise any of the $V_L$ regions VK#1, VK#2, VK#3, or VK#4 as shown in FIG. 1. In some embodiments, the antibody has a $V_H$ region VH#1, VH#2, VH#3, VH#4, or VH#5 as shown in FIG. 1; and a $V_L$ region VK#1, VK#2, VK#3, or VK#4 as shown in FIG. 1.

An antibody may be tested to confirm that the antibody retains the activity of antagonizing GM-CSF activity. The antagonist activity can be determined using any number of endpoints, including proliferation assays. Anti-GM-CSF antibodies may be evaluated using any number of assays that assess GM-CSF function. For example, cell-based assays for GM-CSF receptor signaling, such as assays which determine the rate of proliferation of a GM-CSF-dependent cell line in response to a limiting amount of GM-CSF, are conveniently used. The human TF-1 cell line is suitable for use in such an assay. See, Krinner et al., (2007) Mol. Immunol. An antibody that is administered to treat a disease for which it is desirable to inhibit GM-CSF preferably retains at least about 50%, or at least about 75%, 80%, 90%, 95%, or 100%, of the antagonist activity of the antibody chimeric c19/2, e.g., WO03/068920, which has the variable regions of the mouse monoclonal antibody LMM102 and the CDRs, as defined by Kabat:

```
CDRH1    DYNIH            (SEQ ID NO: 35)

CDRH2    YIAPYSGGTGYNQEFKN (SEQ ID NO: 36)

CDRH3    RDRFPYYFDY       (SEQ ID NO: 16)

CDRL1    KASQNVGSNVA      (SEQ ID NO: 37)

CDRL2    SASYRSG          (SEQ ID NO: 38)

CDRL3    QQFNRSPLT        (SEQ ID NO: 28).
```

A high-affinity antibody may be identified using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor. An antibody of the invention typically binds with similar affinity to both glycosylated and non-gycosylated from of GM-CSF.

Antibodies of the invention compete with c19/2 for binding to GM-CSF. The ability of an antibody described herein to block or compete with c19/2 for binding to GM-CSF indicates that the antibody binds to the same epitope c19/2 or to an epitope that is close to, e.g., overlapping, with the epitope that is bound by c19/2. In other embodiments an antibody described herein, e.g., an antibody comprising a $V_H$ and $V_L$ region combination as shown in the table provided in FIG. 1, can be used as a reference antibody for assessing whether another antibody competes for binding to GM-CSF. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays, such as immunoblots.

Methods for the isolation of antibodies with V-region sequences close to human germ-line sequences have previously been described (US patent application publication nos. 20050255552 and 20060134098). Antibody libraries may be expressed in a suitable host cell including mammalian cells, yeast cells or prokaryotic cells. For expression in some cell systems, a signal peptide can be introduced at the N-terminus to direct secretion to the extracellular medium. Antibodies may be secreted from bacterial cells such as E. coli with or without a signal peptide. Methods for signal-less secretion of antibody fragments from E. coli are described in US patent application 20070020685.

To generate a GM-CSF-binding antibody, one of the $V_H$-regions of the invention, e.g., shown in FIG. 1, is combined with one of the $V_L$-regions of the invention, e.g., shown in FIG. 1, and expressed in any of a number of formats in a suitable expression system. Thus the antibody may be expressed as a scFv, Fab, Fab' (containing an immunoglobulin hinge sequence), F(ab')$_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems. Each of the $V_H$-regions described herein may be paired with each of the $V_L$ regions to generate an anti-GM-CSF antibody. Exemplary combinations of heavy and light chains are shown in the table in FIG. 1.

The antibodies of the invention inhibit GM-CSF receptor activation, e.g., by inhibiting GM-CSF binding to the receptor, and exhibit high affinity binding to GM-CSF, e.g., 500 pM. In some embodiments, the antibody has a dissociation constant of about $10^{-4}$ per sec or less. Not to be bound by theory, an antibody with a slower dissociation constant provides improved therapeutic benefit. For example, an antibody of the invention that has a three-fold slower off-rate than c19/2, produced a 10-fold more potent GM-CSF neutralizing activity, e.g., in a cell-based assay such as IL-8 production (see, e.g., Example 2).

Antibodies may be produced using any number of expression systems, including both prokaryotic and eukaryotic expression systems. In some embodiments, the expression system is a mammalian cell expression, such as a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a discistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention may be produced in any number of formats, including as a Fab, a Fab', a F(ab')$_2$, a scFv, or a dAB. An antibody of the invention can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA.

In some embodiments of the invention, the antibody $V_L$ region, e.g., VK#1, VK#2, VK#3, or VK#4 of FIG. 1, is combined with a human kappa constant region (e.g., SEQ ID NO:10) to form the complete light-chain.

In some embodiments of the invention, the $V_H$ region is combined a human gamma-1 constant region. Any suitable gamma-1 f allotype can be chosen, such as the f-allotype. Thus, in some embodiments, the antibody is an IgG having an f-allotype constant region, e.g., SEQ ID NO:11, that has a $V_H$ selected from VH#1, VH#2, VH#3, VH#4, or VH#5 (FIG. 1). In some embodiments, the antibody has a $V_L$ selected from VK#1, VK#2, VK#3, or VK#4 (FIG. 1.) In particular embodiments, the antibody has a kappa constant region as set forth in SEQ ID NO:10, and a heavy chain constant region as set forth in SEQ ID NO:11, where the heavy and light chain variable regions comprise one of the following combinations from the sequences set forth in FIG. 1: a) VH#2, VK#3; b) VH#1, VK#3; c) VH#3, VK#1; d) VH#3, VL#3; e) VH#4, VK#4; f) VH#4, VK#2; g) VH#5, VK#1; h) VH#5, VK#2; i) VH#3, VK#4; or j) VH#3, VL#3).

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the antibodies of the invention are in the form of a Fab' fragment. A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class.

V. Administration of Anti-GM-CSF Antibodies for the Treatment of Diseases in which GM-CSF is a Target.

The invention also provides methods of treating a patient that has a disease involving GM-CSF in which it is desirable to inhibit GM-CSF activity, i.e., in which GM-CSF is a therapeutic target. In some embodiments, such a patient has a chronic inflammatory disease, e.g., arthritis, e.g., rheumatoid arthritis, psoriatic arthritis, ankylosing spondylitis, juvenile idiopathic arthritis, and other inflammatory diseases of the joint; inflammatory bowel diseases, e.g., ulcerative colitis, Crohn's disease, Barrett's syndrome, ileitis, enteritis, and gluten-sensitive enteropathy; inflammatory disorders of the respiratory system, such as asthma, adult respiratory distress syndrome, allergic rhinitis, silicosis, chronic obstructive pulmonary disease, hypersensitivity lung diseases, bronchiectasis; inflammatory diseases of the skin, including psoriasis, scleroderma, and inflammatory dermatoses such as eczema, atopic dermatitis, urticaria, and pruritis; disorders involving inflammation of the central and peripheral nervous system, including multiple sclerosis, idiopathic demyelinating polyneuropathy, Guillain-Barre syndrome, chronic inflammatory demyelinating polyneuropathy, and neurodegenerative diseases such as Alzheimer's disease. Various other inflammatory diseases can be treated using the methods of the invention. These include systemic lupus erythematosis, immune-mediated renal disease, e.g., glomerulonephritis, and spondyloarthropathies; and diseases with an undesirable chronic inflammatory component such as systemic sclerosis, idiopathic inflammatory myopathies, Sjogren's syndrome, vasculitis, sarcoidosis, thyroiditis, gout, otitis, conjunctivitis, sinusitis, sarcoidosis, Behcet's syndrome, hepatobiliary diseases such as hepatitis, primary biliary cirrhosis, granulomatous hepatitis, and sclerosing cholangitis. In some embodiments, the patient has inflammation following injury to the cardiovascular system. Various other inflammatory diseases include tuberculosis and chronic cholecystitis. Additional chronic inflammatory diseases are described, e.g., in Harrison's Principles of Internal Medicine, 12th Edition, Wilson, et al., eds., McGraw-Hill, Inc.). In some embodiments, a patient treated with an antibody has a cancer in which GM-CSF contributes to tumor or cancer cell growth, e.g., acute myeloid leukemia. In some embodiments, a patient treated with an antibody of the invention has, or is at risk of heart failure, e.g., due to ischemic injury to the cardiovascular system such as ischemic heart disease, stroke, and atherosclerosis. In some embodiments, a patient treated with an antibody of the invention has asthma. In some embodiments, a patient treated with an antibody of the invention has Alzheimer's disease. In some embodiments, a patient treated with an antibody of the invention has osteopenia, e.g., osteoporosis. In some embodiments, a patient treated with an antibody of the invention has thrombocytopenia purpura. In some embodiments, the patient has Type I or Type II diabetes. In some embodiments, a patient may have more than one disease in which GM-CSF is a therapeutic target, e.g., a patient may have rheumatoid arthritis and heart failure, or osteoporosis and rheumatoid arthritis, etc.

The methods of the invention comprise administering an anti-GM-CSF antibody as a pharmaceutical composition to a patient in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005.

The anti-GM-CSF antibody is provided in a solution suitable for injection into the patient such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient, e.g., a patient that has osteopenia, asthma, rheumatoid arthritis, psoriatic arthritis, ankylosing spondylitis, juvenile idiopathic arthritic, polymyositis, systemic lupus erythrematosus, heart failure, cardiac damage, e.g., following a heart attack, thrombocytopenia purpura, or diabetes, in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of the disease in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of anti-GM-CSF antibody to effectively treat the patient.

The antibody may be administered alone, or in combination with other therapies to treat the disease of interest.

The antibody can be administered by injection or infusion through any suitable route including but not limited to intravenous, sub-cutaneous, intramuscular or intraperitoneal routes. In some embodiments, the antibody may be administered by insufflation. In an exemplary embodiment, the antibody may be stored at 10 mg/ml in sterile isotonic aqueous saline solution for injection at 4° C. and is diluted in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. Preferably the dose is in the range 1-10 mg/kg or approximately 50 mg-1000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months. In other embodiments, the antibody is administered approximately once per month.

A $V_H$ region and/or $V_L$ region of the invention may also be used for diagnostic purposes. For example, the $V_H$ and/or $V_L$ region may be used for clinical analysis, such as detection of GM-CSF levels in a patient. A $V_H$ or $V_L$ region of the invention may also be used, e.g., to produce anti-Id antibodies.

EXAMPLES

Example 1

Identification of Engineered Human Anti-GM-CSF V Regions

Humaneering was performed as described in US patent application publication no. 20050255552. Epitope-focused libraries were constructed from human V-segment library sequences linked to a CDR3-FR4 region containing BSD sequences in CDRH3 and CDRL3 together with human germ-line J-segment sequences. For the heavy chain, human germ-line JH4 sequence was used and for the light chain, human germ-line JK4 sequence was used.

Full-length Humaneered V-regions from a Vh1-restricted library were selected that supported binding to recombinant human GM-CSF. The "full-length" V-kappa library was used as a base for construction of "cassette" libraries as described in US patent application publication no. 20060134098, in which only part of the murine c19/2 V-segment was initially replaced by a library of human sequences. Two types of cassettes were constructed. Cassettes for the V-kappa chains were made by bridge PCR with overlapping common sequences within the framework 2 region. In this way "front-end" and "middle" human cassette libraries were constructed for the human V-kappa III isotype. Human V-kappa III cassettes which supported binding to GM-CSF were identified by colony-lift binding assay and ranked according to affinity in ELISA. The V-kappa human "front-end" and "middle" cassettes were fused together by bridge PCR to reconstruct a fully human V-kappa region that supported GM-CSF binding activity. The Humaneered Fabs thus consist of Humaneered V-heavy and V-kappa regions that support binding to human GM-CSF.

Binding activity was determined by surface plasmon resonance (spr) analysis. Biotinylated GM-CSF was captured on a streptavidin-coated CM5 biosensor chip. Humaneered Fab fragments expressed from E. Coli were diluted to a starting concentration of 30 nM in 10 mM HEPES, 150 mM NaCl, 0.1 mg/ml BSA and 0.005% P20 at pH 7.4. Each Fab was diluted 4 times using a 3-fold dilution series and each concentration was tested twice at 37° C. to determine the binding kinetics with the different density antigen surfaces. The data from all three surfaces were fit globally to extract the dissociation constants.

Exemplary humaneered anti-GM-CSF V regions are shown in FIG. 1.

Example 2

Evaluation of a Humaneered GM-CSF Antibody

This example evaluates the binding activity and biological potency of a humaneered anti-GM-CSF antibody in a cell-based assay in comparison to a chimeric IgG1k antibody (Ab2) having variable regions from the mouse antibody LMM102 (Nice et al., Growth Factors 3:159, 1990). Ab1 is a humaneered IgG1k antibody against GM-CSF having identical constant regions to Ab2.

Surface Plasmon Resonance Analysis of Binding of Human GM-CSF to Ab1 and Ab2

Surface Plasmon resonance analysis was used to compare binding kinetics and monovalent affinities for the interaction of Ab1 and Ab2 with glycosylated human GM-CSF using a Biacore 3000 instrument. Ab1 or Ab2 was captured onto the Biacore chip surface using polyclonal anti-human F(ab')2. Glycosylated recombinant human GM-CSF expressed from human 293 cells was used as the analyte. Kinetic constants were determined in 2 independent experiments (see FIG. 2 and Table 1). The results show that GM-CSF bound to Ab2 and Ab1 with comparable monovalent affinity in this experiment. However, Ab1 had a two-fold slower "on-rate" than Ab2, but an "off-rate" that was approximately three-fold slower.

TABLE 1

Kinetic constants at 37° C. determined from the surface plasmon resonance analysis in FIG. 2; association constant ($k_a$), dissociation constant ($k_d$) and calculated affinity (KD) are shown.

| | $k_a$ (M$^{-1}$s$^{-1}$) | $k_d$ (s$^{-1}$) | KD (pM) |
|---|---|---|---|
| Ab2 | 7.20 × 10$^5$ | 2.2 × 10$^{-5}$ | 30.5 |
| Ab1 | 2.86 × 10$^5$ | 7.20 × 10$^{-6}$ | 25.1 |

Figure 3:
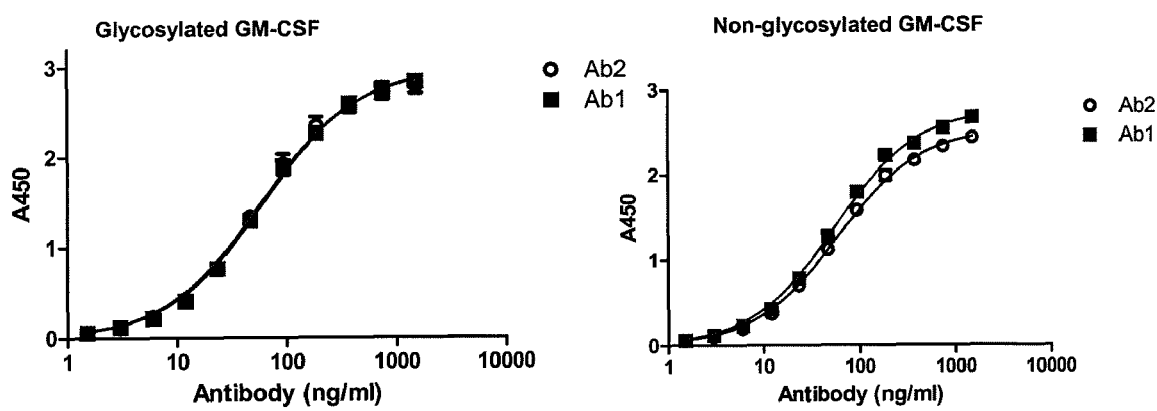
FIG. 3. Binding of Ab1 and Ab2 to glycosylated and non-glycosylated GM-CSF. Binding to glycosylated GM-CSF expressed from human 293 cells or non-glycosylated GM-CSF expressed in *E. coli* was determined by ELISA. Representative results from a single experiment are shown (exp 1). Two-fold dilutions of Ab1 and Ab2 starting from 1500 ng/ml were applied to GM-CSF coated wells. Each point represents mean±standard error for triplicate determinations. Sigmoidal curve fit was performed using Prism 5.0 Software (Graphpad).

GM-CSF is naturally glycosylated at both N-linked and O-linked glycosylation sites although glycosylation is not required for biological activity. In order to determine whether GM-CSF glycosylation affects the binding of Ab1 or Ab2, the antibodies were compared in an ELISA using recombinant GM-CSF from two different sources; GM-CSF expressed in E. coli (non-glycosylated) and GM-CSF expressed from human 293 cells (glycosylated). The results in FIG. 3 and Table 2 showed that both antibodies bound glycosylated and non-glycosylated GM-CSF with equivalent activities. The two antibodies also demonstrated comparable $EC_{50}$ values in this assay.

TABLE 2

Summary of $EC_{50}$ for binding of Ab2 and Ab1 to human GM-CSF from two different sources determined by ELISA.

|     | Non-glycosylated (exp 1) | Non-glycosylated (exp 2) | Glycosylated (exp 1) |
|-----|--------------------------|--------------------------|----------------------|
| Ab2 | 400 pM                   | 433 pM                   | 387 pM               |
| Ab1 | 373 pM                   | 440 pM                   | 413 pM               |

Figure 5:
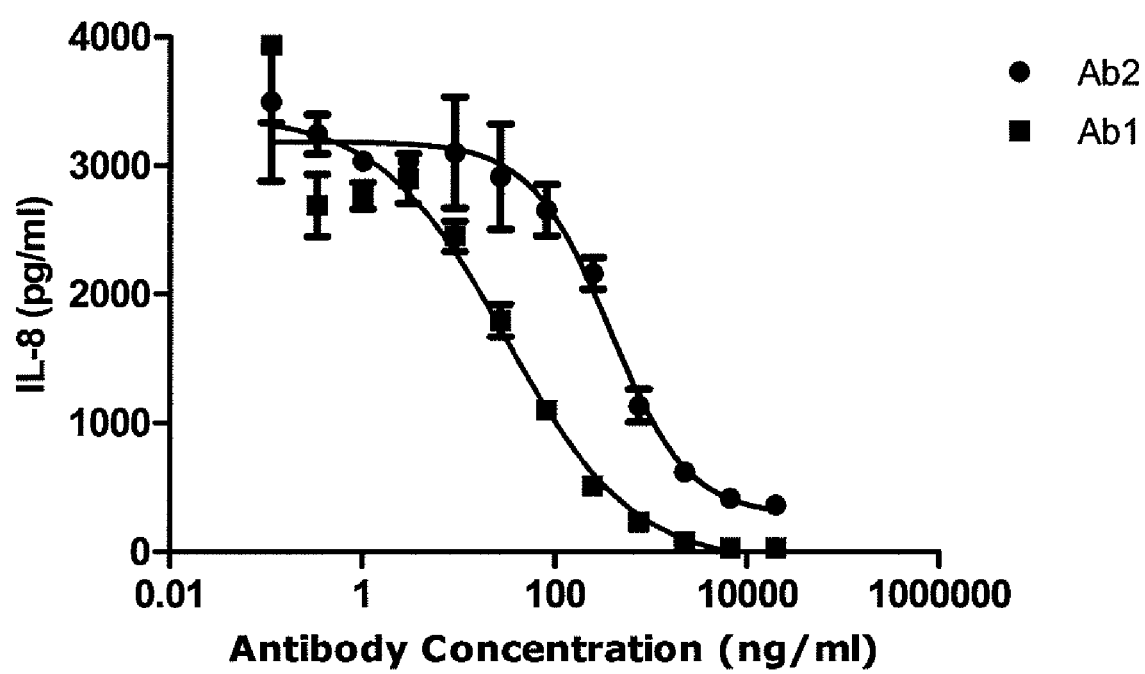
FIG. 5. Inhibition of GM-CSF-induced IL-8 expression. Various amounts of each antibody were incubated with 0.5 ng/ml GM-CSF and incubated with U937 cells for 16 hrs. IL-8 secreted into the culture supernatant was determined by ELISA

Binding to recombinant GM-CSF from human 293 cells (glycosylated) or from *E. coli* (non-glycosylated) was determined from two independent experiments. Experiment 1 is shown in FIG. 5.

Ab1 is a humaneered antibody that was derived from the mouse variable regions present in Ab2. Ab1 was tested for overlapping epitope specificity (Ab2) by competition ELISA.

Figure 4:
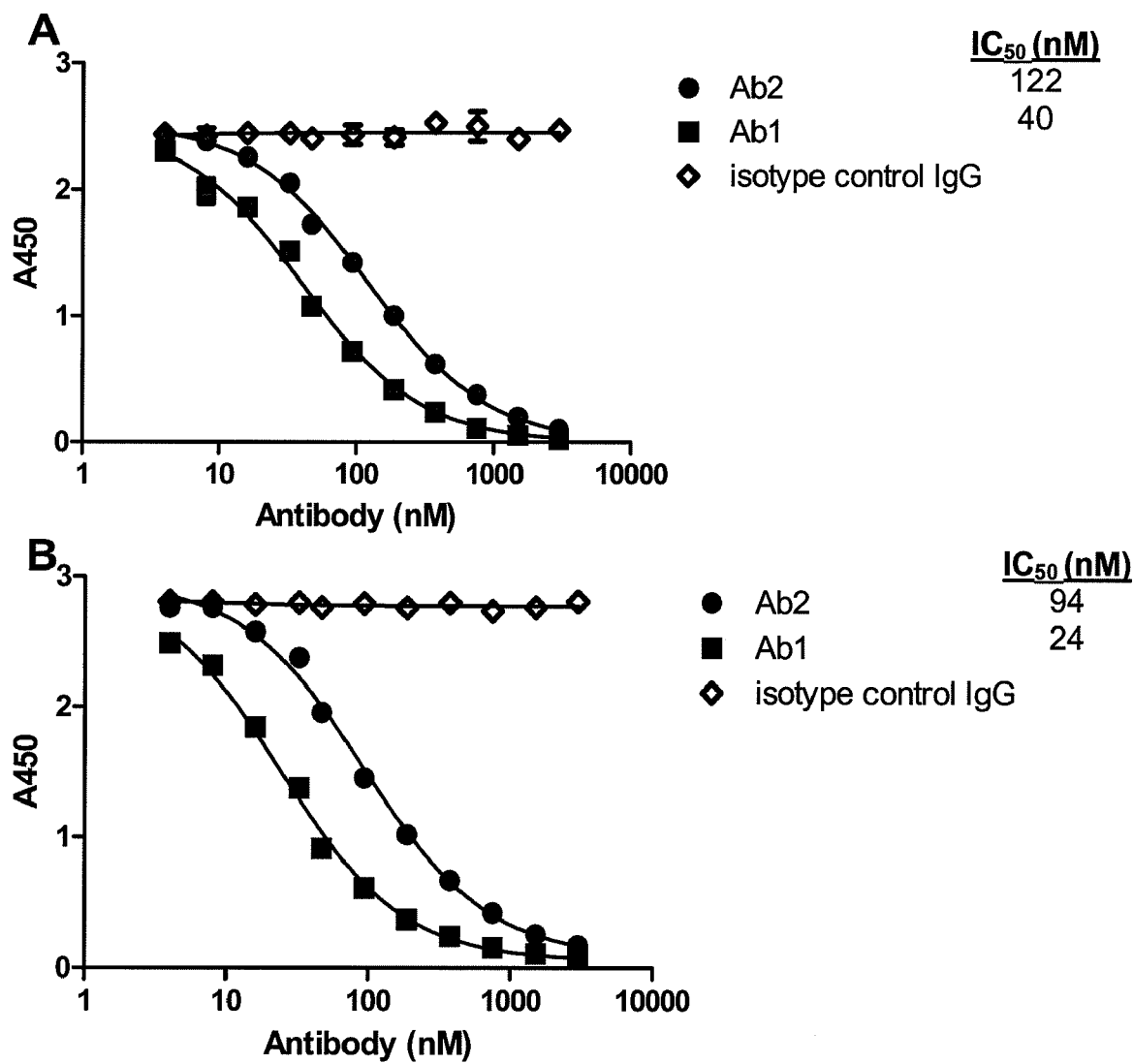
FIG. 4. Competition ELISA demonstrating binding of Ab1 and Ab2 to a shared epitope. ELISA plates coated with 50 ng/well of recombinant GM-CSF were incubated with various concentrations of antibody (Ab2, Ab1 or isotype control antibody) together with 50 nM biotinylated Ab2. Biotinylated antibody binding was assayed using neutravidin-HRP conjugate. Competition for binding to GM-CSF was for 1 hr (A) or for 18 hrs (B). Each point represents mean±standard error for triplicate determinations. Sigmoidal curve fit was performed using Prism 5.0 Software (Graphpad).

Biotinylated Ab2 was prepared using known techniques. Biotinylation did not affect binding of Ab2 to GM-CSF as determined by ELISA. In the assay, Ab2 or Ab1 was added in varying concentrations with a fixed amount of biotinylated Ab2. Detection of biotinylated Ab2 was assayed in the presence of unlabeled Ab or Ab1 competitor (FIG. 4). Both Ab1 and Ab2 competed with biotinylated Ab2 for binding to GM-CSF, thus indicating binding to the same epitope. Ab1 competed more effectively for binding to GM-CSF than Ab2, consistent with the slower dissociation kinetics for Ab1 when compared with Ab2 by surface plasmon resonance analysis.

Neutralization of GM-CSF Activity by Ab1 and Ab2

A cell based assay for neutralization of GM-CSF activity was employed to evaluate biological potency. The assay measures IL-8 secretion from U937 cells induced with GM-CSF. IL-8 secreted into the culture supernatant is determined by ELISA after 16 hours induction with 0.5 ng/ml *E. coli*-derived GM-CSF.

A comparison of the neutralizing activity of Ab1 and Ab2 in this assay is shown in a representative assay in FIG. 5. In three independent experiments, Ab1 inhibited GM-CSF activity more effectively than Ab2 when comparing $IC_{50}$ (Table 3).

TABLE 3

Comparison of IC50 for inhibition of GM-CSF induced IL-8 expression.

| Experiment | Ab2 (ng/ml) | Ab2 (nM) | Ab1 (ng/ml) | Ab1 (nM) |
|------------|-------------|----------|-------------|----------|
| A          | 363         | 2.4      | 31.3        | 0.21     |
| B          | 514         | 3.4      | 92.5        | 0.62     |
| C          | 343         | 2.2      | 20.7        | 0.14     |
| Mean       | 407         | 2.7      | 48.2        | 0.32     |

Data from three independent experiments shown in FIG. 5 and mean $IC_{50}$ are expressed in ng/ml and nM.

Summary

The humaneered Ab1 bound to GM-CSF with a calculated equilibrium binding constant (KD) of 25 pM. Ab2 bound to GM-CSF with a KD of 30.5 pM. Ab2 showed a two-fold higher association constant ($k_a$) than Ab1 for GM-CSF while Ab1 showed three-fold slower dissociation kinetics ($k_d$) than Ab2. Ab2 and Ab1 showed similar binding activity for glycosylated and non-glycosylated GM-CSF in an antigen-binding ELISA. A competition ELISA confirmed that both antibodies competed for the same epitope; Ab1 showed higher competitive binding activity than Ab2. In addition, Ab1 showed higher GM-CSF neutralization activity than Ab2 in a GM-CSF-induced IL-8 induction assay.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Exemplary $V_H$ region sequences of anti-GM-CSF antibodies of the invention:
SEQ ID NO: 1
(VH#1, FIG. 1)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCVRRD

RFPYYFDYWGQGTLVTVSS

SEQ ID NO: 2
(VH#2, FIG. 1)
QVQLVQSGAEVKKPGASVKVSCKASGYSFTNYYIHWVRQAPGQRLEWMGW

INAGNGNTKYSQKFQGRVAITRDTSASTAYMELSSLRSEDTAVYYCARRD

RFPYYFDYWGQGTLVTVSS

SEQ ID NO: 3
(VH#3, FIG. 1)
QVQLVQSGAEVKKPGASVKVSCKASGYSFTNYYIHWVRQAPGQRLEWMGW

INAGNGNTKYSQKFQGRVAITRDTSASTAYMELSSLRSEDTAVYYCARRQ

RFPYYFDYWGQGTLVTVSS

SEQ ID NO: 4
(VH#4, FIG. 1)
QVQLVQSGAEVKKPGASVKVSCKASGYSFTNYYIHWVRQAPGQRLEWMGW

INAGNGNTKYSQKFQGRVAITRDTSASTAYMELSSLRSEDTAVYYCVRRQ

RFPYYFDYWGQGTLVTVSS

SEQ ID NO: 5
(VH#5, FIG. 1)
QVQLVQSGAEVKKPGASVKVSCKASGYSFTNYYIHWVRQAPGQRLEWMGW

INAGNGNTKYSQKEQGRVTITRDTSASTAYMELSSLRSEDTAVYYCVRRQ

RFPYYFDYWGQGTLVTVSS

Exemplary $V_L$ region sequences of anti-GM-CSF antibodies of the invention:
SEQ ID NO: 6
(VK#1, FIG. 1)
EIVLTQSPATLSVSPGERATLSCRASQSVGTNVAWYQQKPGQAPRVLIYS

TSSRATGITDRFSGSGSGTDFTLTISRLEPEDFAVYYCQQFNRSPLTFGG

GTKVEIK

SEQ ID NO: 7
(VK#2, FIG. 1)
EIVLTQSPATLSVSPGERATLSCRASQSVGTNVAWYQQKPGQAPRVLIYS

TSSRATGITDRFSGSGSGTDFTLTISRLEPEDFAVYYCQQFNKSPLTFGG

GTKVEIK

SEQ ID NO: 8
(VK#3, FIG. 1)
EIVLTQSPATLSVSPGERATLSCRASQSIGSNLAWYQQKPGQAPRVLIYS

TSSRATGITDRFSGSGSGTDFTLTISRLEPEDFAVYYCQQFNRSPLTFGG

GTKVEIK

SEQ ID NO: 9
(VK#4, FIG. 1)
EIVLTQSPATLSVSPGERATLSCRASQSIGSNLAWYQQKPGQAPRVLIYS

TSSRATGITDRFSGSGSGTDFTLTISRLEPEDFAVYYCQQFNKSPLTFGG

GTKVEIK

SEQ ID NO: 10
Exemplary kappa constant region
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

SEQ ID NO: 11
Exemplary heavy chain constant region, f-allotype:
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

---

What is claimed is:

1. An isolated anti-GM-CSF antibody, comprising:
a $V_H$ that has a CDR1 having a sequence NYYIH (SEQ ID NO:25), a CDR2 having a sequence WINAGNGNT-KYSQKFQG (SEQ ID NO:27), and a CDR3 having a sequence RQRFPYYFDY (SEQ ID NO:16); and
a $V_L$ that has a CDR1 having a sequence RASQSVGTNVA (SEQ ID NO:31) or RASQSIGSNLA (SEQ ID NO:32), a CDR2 having a sequence STSSRAT (SEQ ID NO:33), and a CDR3 having a sequence QQFNKSPLT (SEQ ID NO:18) or QQFNRSPLT (SEQ ID NO:28).

2. The antibody of claim 1, wherein the J segment comprises YFDYWGQGTLVTVSS (SEQ ID NO:14).

3. The antibody of claim 1, wherein the $V_H$ region comprises a V-segment sequence from a $V_H$ region VH#3 (SEQ ID NO:3), VH#4 (SEQ ID NO:4), or VH#5 (SEQ ID NO:5).

4. The antibody of claim 1, wherein the $V_H$ has the sequence of VH#3 (SEQ ID NO:3), VH#4 (SEQ ID NO:4), or VH#5 (SEQ ID NO:5).

5. The antibody of claim 1, wherein the antibody comprises a human germline JK4 region.

6. The antibody of claim 1, wherein the $V_L$ region CDR3 comprises QQFNKSPLT (SEQ ID NO:18).

7. The antibody of claim 6, wherein the $V_L$ region CDR1 has the sequence RASQSIGSNLA (SEQ ID NO:32).

8. The antibody of claim 1, wherein the $V_L$ region CDR3 comprises QQFNRSPLT (SEQ ID NO:28).

9. The antibody of claim 8, wherein the $V_L$ region CDR1 has the sequence RASQSVGTNVA (SEQ ID NO:31).

10. The antibody of claim 1, wherein the $V_L$ region comprises a V segment sequence from a $V_L$ region VK#1 (SEQ ID NO:6), VK#2 (SEQ ID NO:7), VK#3 (SEQ ID NO:8), or VK#4 (SEQ ID NO:9).

11. The antibody of claim 1, wherein the $V_L$ region has the sequence of VK#1 (SEQ ID NO:6), VK#2 (SEQ ID NO:7), VK#3 (SEQ ID NO:8), or VK#4 (SEQ ID NO:9).

12. The antibody of claim 1, wherein the antibody is an IgG.

13. The antibody of claim 12, wherein the antibody comprises a heavy chain constant region having the amino acid sequence set forth in SEQ ID NO:11.

14. The antibody of claim 1, wherein the antibody comprises a kappa light chain constant region having the amino acid sequence set forth in SEQ ID NO:10.

15. The antibody of claim 1, wherein the $V_H$ region or the $V_L$ region, or both the $V_H$ and $V_L$ region amino acid sequences comprise a methionine at the N-terminus.

16. The antibody of claim 1, wherein the antibody comprises a $V_H$ region having a sequence of VH#3 (SEQ ID NO:3), VH#4 (SEQ ID NO:4), or VH#5 (SEQ ID NO:5) and a $V_L$ region having a sequence of VK#1 (SEQ ID NO:6), VK#2 (SEQ ID NO:7), VK#3 (SEQ ID NO:8), or VK#4 (SEQ ID NO:9).

17. The antibody of claim 16, wherein the antibody is an IgG.

18. The antibody of claim 17, wherein the antibody comprises a heavy chain constant region having the amino acid sequence set forth in SEQ ID NO:11.

19. The antibody of claim 16, wherein the antibody comprises a kappa light chain constant region having the amino acid sequence set forth in SEQ ID NO:10.

20. The antibody of claim 1, wherein the antibody has:
a heavy chain and a light chain variable region combination selected from the group consisting of:
a) VH#4 (SEQ ID NO:4), VK#1 (SEQ ID NO:6);
b) VH#4 (SEQ ID NO:4), VK#2 (SEQ ID NO:7;
c) VH#4 (SEQ ID NO:4), VK#3 (SEQ ID NO:8)
d) VH#4 (SEQ ID NO:4), VK#4 (SEQ ID NO:9);
e) VH#5 (SEQ ID NO:5), VK#1 (SEQ ID NO:6);
f) VH#5 (SEQ ID NO:5), VK#2 (SEQ ID NO:7;
g) VH#5 (SEQ ID NO:5), VK#3 (SEQ ID NO:8); and
d) VH#5 (SEQ ID NO:5), VK#4 (SEQ ID NO:9).

21. The antibody of claim 20, wherein the heavy chain variable region is VH#4 (SEQ ID NO:4) and the light chain variable region is VK#1 (SEQ ID NO:6).

22. The antibody of claim 20, wherein the heavy chain variable region is VH#4 (SEQ ID NO:4) and the light chain variable region is VK#2 (SEQ ID NO:7).

23. The antibody of claim 20, wherein the heavy chain variable region is VH#4 (SEQ ID NO:4) and the light chain variable region is VK#3 (SEQ ID NO:8).

24. The antibody of claim 20, wherein the heavy chain variable region is VH#4 (SEQ ID NO:4) and the light chain variable region is VK#4 (SEQ ID NO:9).

25. The antibody of claim 20, wherein the heavy chain variable region is VH#5 (SEQ ID NO:5) and the light chain variable region is VK#1 (SEQ ID NO:6).

26. The antibody of claim 20, wherein the heavy chain variable region is VH#5 (SEQ ID NO:5) and the light chain variable region is VK#2 (SEQ ID NO:7).

27. The antibody of claim 20, wherein the heavy chain variable region is VH#5 (SEQ ID NO:5) and the light chain variable region is VK#3 (SEQ ID NO:8).

28. The antibody of claim 20, wherein the heavy chain variable region is VH#5 (SEQ ID NO:5) and the light chain variable region is VK#4 (SEQ ID NO:9).

29. The antibody of claim 20, wherein the antibody comprises a heavy chain constant region having the amino acid sequence set forth in SEQ ID NO:11.

30. The antibody of claim 29, wherein the antibody comprises a kappa light chain constant region having the amino acid sequence set forth in SEQ ID NO:10.

31. An isolated anti-GM-CSF antibody comprising a $V_H$ region and a $V_L$ region, wherein the $V_H$ region has the amino acid sequence set forth in SEQ ID NO:1, SEQ ID NO:2, SEQ ID NO:3, SEQ ID NO:4, or SEQ ID NO:5.

32. The isolated antibody of claim 31 wherein the antibody comprises the $V_H$ region set forth in SEQ ID NO:5.

33. The isolated antibody of claim 31 wherein the antibody comprises the $V_H$ region set forth in SEQ ID NO:4.

34. The isolated antibody of claim 31 wherein the antibody comprises the $V_H$ region set forth in SEQ ID NO:3.

35. The isolated antibody of claim 31 wherein the antibody comprises the $V_H$ region set forth in SEQ ID NO:2.

36. The isolated antibody of claim 31 wherein the antibody comprises the $V_H$ region set forth in SEQ ID NO:1.

* * * * *

SEQUENCE LISTING

<160> NUMBER OF SEQ ID NOS: 39

<210> SEQ ID NO 1
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody heavy
      chain variable region (VH) VH#1

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Arg Asp Arg Phe Pro Tyr Tyr Phe Asp Tyr Trp Gly Gln Gly
            100                 105                 110

Thr Leu Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody heavy
      chain variable region (VH) VH#2

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr

```
                    20                  25                  30

Tyr Ile His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Arg Phe Pro Tyr Tyr Phe Asp Tyr Trp Gly Gln Gly
            100                 105                 110

Thr Leu Val Thr Val Ser Ser
            115

<210> SEQ ID NO 3
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody heavy
      chain variable region (VH) VH#3

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Arg Phe Pro Tyr Tyr Phe Asp Tyr Trp Gly Gln Gly
            100                 105                 110

Thr Leu Val Thr Val Ser Ser
            115

<210> SEQ ID NO 4
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody heavy
      chain variable region (VH) VH#4

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60
```

```
Gln Gly Arg Val Ala Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody heavy
      chain variable region (VH) VH#5

<400> SEQUENCE: 5

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ser Phe Thr Asn Tyr
                 20                  25                  30

Tyr Ile His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody kappa
      light chain variable region (VL) VK#1

<400> SEQUENCE: 6

Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Gly Thr Asn
                 20                  25                  30

Val Ala Trp Tyr Gln Gln Lys Pro Gly Gln Ala Pro Arg Val Leu Ile
             35                  40                  45

Tyr Ser Thr Ser Ser Arg Ala Thr Gly Ile Thr Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Phe Asn Arg Ser Pro Leu
                 85                  90                  95

Thr Phe Gly Gly Gly Thr Lys Val Glu Ile Lys
            100                 105
```

<210> SEQ ID NO 7
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody kappa
      light chain variable region (VL) VK#2

<400> SEQUENCE: 7

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody kappa
      light chain variable region (VL) VK#3

<400> SEQUENCE: 8

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (GM-CSF) antibody kappa
      light chain variable region (VL) VK#4

<400> SEQUENCE: 9

Glu Ile Val Leu Thr Gln Ser Pro Ala Thr Leu Ser Val Ser Pro Gly

```
                1               5                   10                  15
Glu Arg Ala Thr Leu Ser Cys Arg Ala Ser Gln Ser Ile Gly Ser Asn
                    20                  25                  30

Leu Ala Trp Tyr Gln Gln Lys Pro Gly Gln Ala Pro Arg Val Leu Ile
            35                  40                  45

Tyr Ser Thr Ser Ser Arg Ala Thr Gly Ile Thr Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: synthetic kappa constant region

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 330
<212> TYPE: PRT
<213> ORGANISM: Artificial Sequence
<220> FEATURE:
<223> OTHER INFORMATION: synthetic f-allotype heavy chain constant
      region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)
      binding specificity determinant (BSD)

<400> SEQUENCE: 12

Arg Gln Arg Phe Pro Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)
      binding specificity determinant (BSD)

<400> SEQUENCE: 13

Arg Asp Arg Phe Pro Tyr
1               5

<210> SEQ ID NO 14
<211> LENGTH: 15
<212> TYPE: PRT
<213> ORGANISM: Artificial Sequence
```

```
<220> FEATURE:
<223> OTHER INFORMATION: synthetic heavy chain variable region (VH)
      human J-segment JH4

<400> SEQUENCE: 14

Tyr Phe Asp Tyr Trp Gly Gln Gly Thr Leu Val Thr Val Ser Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)

<400> SEQUENCE: 15

Arg Gln Arg Phe Pro Tyr Tyr Phe Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)

<400> SEQUENCE: 16

Arg Asp Arg Phe Pro Tyr Tyr Phe Asp Tyr
1               5                   10

<210> SEQ ID NO 17
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)
<221> NAME/KEY: VARIANT
<222> LOCATION: (5)...(5)
<223> OTHER INFORMATION: Xaa = Lys or Arg

<400> SEQUENCE: 17

Gln Gln Phe Asn Xaa Ser Pro Leu Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)

<400> SEQUENCE: 18

Gln Gln Phe Asn Lys Ser Pro Leu Thr
1               5

<210> SEQ ID NO 19
<211> LENGTH: 98
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: human germline heavy chain variable region VH1
      1-02

<400> SEQUENCE: 19
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 20
<211> LENGTH: 98
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: human germline heavy chain variable region VH1
      1-03

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 21
<211> LENGTH: 96
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: human germline kappa light chain variable
      region VKIII A27

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Ser Ser Pro
                    85                  90                  95

<210> SEQ ID NO 22
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)
<221> NAME/KEY: VARIANT
<222> LOCATION: (2)...(2)
<223> OTHER INFORMATION: Xaa = Gln or Asp

<400> SEQUENCE: 22

Arg Xaa Arg Phe Pro Tyr
1               5

<210> SEQ ID NO 23
<211> LENGTH: 21
<212> TYPE: PRT
<213> ORGANISM: Artificial Sequence
<220> FEATURE:
<223> OTHER INFORMATION: synthetic combination of heavy chain variable
      region (VH) complementarity-determining region 3
      (CDR3) binding specificity determinant (BSD) and
      human germline J-segment JH4 (CDRH3 and FR4)
<221> NAME/KEY: VARIANT
<222> LOCATION: (2)...(2)
<223> OTHER INFORMATION: Xaa = Gln or Asp

<400> SEQUENCE: 23

Arg Xaa Arg Phe Pro Tyr Tyr Phe Asp Tyr Trp Gly Gln Gly Thr Leu
1               5                   10                  15

Val Thr Val Ser Ser
            20

<210> SEQ ID NO 24
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDR1)

<400> SEQUENCE: 24

Gly Tyr Tyr Met His
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDR1)

<400> SEQUENCE: 25

Asn Tyr Tyr Ile His
1               5

<210> SEQ ID NO 26
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDR2)
```

```
<400> SEQUENCE: 26

Trp Ile Asn Pro Asn Ser Gly Gly Thr Asn Tyr Ala Gln Lys Phe Gln
 1               5                  10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDR2)

<400> SEQUENCE: 27

Trp Ile Asn Ala Gly Asn Gly Asn Thr Lys Tyr Ser Gln Lys Phe Gln
 1               5                  10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)

<400> SEQUENCE: 28

Gln Gln Phe Asn Arg Ser Pro Leu Thr
 1               5

<210> SEQ ID NO 29
<211> LENGTH: 19
<212> TYPE: PRT
<213> ORGANISM: Artificial Sequence
<220> FEATURE:
<223> OTHER INFORMATION: synthetic combination of light chain variable
      region (VL) complementarity-determining region 3
      (CDR3) binding specificity determinant (BSD) and
      human germline J-segment JK4 (CDRL3 and FR4)

<400> SEQUENCE: 29

Gln Gln Phe Asn Arg Ser Pro Leu Thr Phe Gly Gly Gly Thr Lys Val
 1               5                  10                  15

Glu Ile Lys

<210> SEQ ID NO 30
<211> LENGTH: 19
<212> TYPE: PRT
<213> ORGANISM: Artificial Sequence
<220> FEATURE:
<223> OTHER INFORMATION: synthetic combination of light chain variable
      region (VL) complementarity-determining region 3
      (CDR3) binding specificity determinant (BSD) and
      human germline J-segment JK4 (CDRL3 and FR4)

<400> SEQUENCE: 30

Gln Gln Phe Asn Lys Ser Pro Leu Thr Phe Gly Gly Gly Thr Lys Val
 1               5                  10                  15

Glu Ile Lys

<210> SEQ ID NO 31
<211> LENGTH: 11
<212> TYPE: PRT
<213> ORGANISM: Artificial Sequence
<220> FEATURE:
```

-continued

<223> OTHER INFORMATION: synthetic light chain variable region (VL)
      complementarity-determining region 1 (CDR1)

<400> SEQUENCE: 31

Arg Ala Ser Gln Ser Val Gly Thr Asn Val Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDR1)

<400> SEQUENCE: 32

Arg Ala Ser Gln Ser Ile Gly Ser Asn Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: synthetic light chain variable region (VL)
      complementarity-determining region 2 (CDR2)

<400> SEQUENCE: 33

Ser Thr Ser Ser Arg Ala Thr
1               5

<210> SEQ ID NO 34
<211> LENGTH: 10
<212> TYPE: PRT
<213> ORGANISM: Artificial Sequence
<220> FEATURE:
<223> OTHER INFORMATION: synthetic light chain variable region (VL) FR4
      region

<400> SEQUENCE: 34

Phe Gly Gly Gly Thr Lys Val Glu Ile Lys
1               5                   10

<210> SEQ ID NO 35
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDRH1)

<400> SEQUENCE: 35

Asp Tyr Asn Ile His
1               5

<210> SEQ ID NO 36
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDRH2)

<400> SEQUENCE: 36

Tyr Ile Ala Pro Tyr Ser Gly Gly Thr Gly Tyr Asn Gln Glu Phe Lys
1               5                   10                  15

Asn

```
<210> SEQ ID NO 37
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDRL1)

<400> SEQUENCE: 37

Lys Ala Ser Gln Asn Val Gly Ser Asn Val Ala
  1               5                  10

<210> SEQ ID NO 38
<211> LENGTH: 7
<212> TYPE: PRT
<213> ORGANISM: Artificial Sequence
<220> FEATURE:
<223> OTHER INFORMATION: synthetic light chain variable region (VL)
      complementarity-determining region 2 (CDRL2)

<400> SEQUENCE: 38

Ser Ala Ser Tyr Arg Ser Gly
  1               5

<210> SEQ ID NO 39
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDR1)
<221> NAME/KEY: VARIANT
<222> LOCATION: (6)...(6)
<223> OTHER INFORMATION: Xaa = Val or Ile
<221> NAME/KEY: VARIANT
<222> LOCATION: (8)...(8)
<223> OTHER INFORMATION: Xaa = Thr or Ser
<221> NAME/KEY: VARIANT
<222> LOCATION: (10)...(10)
<223> OTHER INFORMATION: Xaa = Val or Leu

<400> SEQUENCE: 39

Arg Ala Ser Gln Ser Xaa Gly Xaa Asn Xaa Ala
  1               5                  10
```